(12) United States Patent
Narula et al.

(10) Patent No.: US 6,340,666 B1
(45) Date of Patent: Jan. 22, 2002

(54) ALLYL ETHER

(75) Inventors: Anubhav P. S. Narula, Hazlet; Edward Arruda, Cliffwood; James Joseph Koestler, Hazlet; Ellen Ann Molner, Kinnelon, all of NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/655,754

(22) Filed: Sep. 6, 2000

(51) Int. Cl.⁷ ............................. A61K 7/46; C07C 43/16
(52) U.S. Cl. ..................... 512/25; 568/687; 510/101; 424/76.2; 424/70.1
(58) Field of Search ................. 568/687, 689; 510/101; 512/25; 424/76.2, 70.1

(56) References Cited

U.S. PATENT DOCUMENTS

| | | | | |
|---|---|---|---|---|
| 3,061,649 A | | 10/1962 | Erickson et al. ............ | 568/687 |
| 3,297,767 A | * | 1/1967 | Leidig et al. ............... | 568/687 |
| 4,534,891 A | | 8/1985 | Boden et al. ........... | 252/522 R |
| 4,931,428 A | * | 6/1990 | Becker et al. ................. | 512/25 |

* cited by examiner

Primary Examiner—Rosalynd Keys
(74) Attorney, Agent, or Firm—Joseph F. Leightner

(57) ABSTRACT

The present invention is directed to 3-hexenyl-2-methylallyl ether and its use in creating perfumes and scents in such items as perfumes, colognes, toilet water and personal care products.

7 Claims, No Drawings

ALLYL ETHER

FIELD OF THE INVENTION

The present invention relates to a new chemical entity and the incorporation of use of the new chemical as a fragrance ingredient

BACKGROUND OF THE INVENTION

There is ongoing need in the fragrance industry to provide new chemicals to give perfumers and other persons of the fragrance industry an ability to create new fragrances for perfumes, colognes and personal care products. Thus there is an ongoing need for creation of new chemicals and the incorporation of these materials in fragrance formulations.

SUMMARY OF THE INVENTION

The present invention provides a novel compound, 3-hexenyl 2-methallyl ether and the incorporation of the compound provides a special fragrance to perfumes, toilet waters, colognes, candles, air fresheners, personal products and the like.

DETAILED DESCRIPTION OF THE INVENTION

The present invention is directed to the compound set forth below.

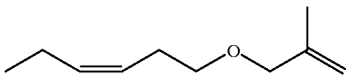

Those with skill in the art will appreciate that there is a sp2 carbon atom (or a double bond) in this molecule which can have either E(trans) or Z(cis) configuration. Both the E and Z isomers of the present invention are contemplated by the claims of the present invention, however from an olfactory perspective the Z form has been found to be more appealing. One method of producing the isomers is through selection of the starting materials. Production of the various isomers is accomplished by the use of standard chemistry (as discussed later). The fragrance of the new chemical has been described as having fresh notes: green, mushroom, fresh cut grass, fruity (rhubarb) and violet.

The compound is obtained by the reaction of hexenol and methyl allyl chloride. For example, if the Z version is desired, then the reaction should be conducted with cis-3-hexenol. Preferably, the reaction is carried out in the presence of sodium hydride and tetrahyrodofuran (THF) as solvents. The reaction is conducted at a temperature of from about 50 to about 70° C.; most preferably at a temperature of about 66° C. One reaction sequence is the mixture of sodium hydride in THF to which the hexenol is added. The methyl allyl chloride is then added to the reaction vessel.

An effective molar ratio of hexenol/methyl allyl chloride employed in carrying out the reaction is approximately 1/1.2. The amount of sodium hydride can range from about 0.1 to 3.0 moles based upon the level of hexenol. Preferably an excess of sodium hydride is employed relative to the hexenol, most preferably from 1.25 to about 1.5 moles relative to the amount of hexenol. When lower levels of sodium hydride are employed the yield of the methyl allyl ether are diminished by as much as 4 percent. The present reaction was capable of yields of greater than 85%, greater than 90% and in a highly preferred embodiment the reaction yield is greater than 95%.

The use of these compounds is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients are known by those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal scents and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in their entirety. Another source of suitable fragrances is found in *Perfumes Cosmetics and Soaps*, Second Edition, edited by W. A. Poucher, 1959. Among the fragrances provided in this treatise are acacia, cassie, chypre, cylamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

Olfactory effective amount is understood to mean the amount of compound in perfume compositions the individual component will contribute its particular olfactory characteristics, but the olfactory effect of the perfume composition will be the sum of the effects of each of the perfume or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art without departing from the scope of this invention. As used herein all percentages are weight percent and g is understood to be grams. All of the materials used to formulate fragrances are available from International Flavor & Fragrances Inc., Hazlet, N.J.

EXAMPLE 1

Reaction to produce 3-hexenyl-2-methylallyl ether

Sodium hydride (60 weight percent, 240 g) and THF were charged to a reaction vessel equipped with a stirring apparatus and reflux condenser, while under a nitrogen blanket. The contents were heated to reflux, approximately 66° C. Hexenol (500 g) was slowly added to the reaction vessel. Hydrogen gas was noted bubbling from the mixture. The contents of the vessel were allowed to continue until no additional hydrogen bubbles were noted.

Methyl allyl chloride (543 g) was added to the reactor contents and the addition was continued until completed. The reaction was allowed to run until completion. The reaction product was isolated using a fractional distillation technique. The product yield was 93 mole % based upon the amount of hexenol employed.

EXAMPLE 2

Two fragrances were made with the following formulations:

| Material | Formulation I | Formulation II |
|---|---|---|
| n-hexyl acetate | 5 | 5 |
| citronenellol coeur | 2 | 2 |
| HEDIONE ™ | 50 | 50 |
| HELIONAL ™ | 5 | 5 |
| Hexenyl acetate | 5 | 5 |
| VERDOX ™ | 5 | 5 |
| Bergamot Oil | 10 | 10 |
| GALAXOLIDE ® (50%) | 100 | 100 |
| Dimethyl-δ-2-benzopyran-3-cyclohexene-1-carboxaldehyde | 1 | 1 |
| Peach Aldehyde Couer (10%) | 1 | 1 |
| PHENOXANAL ® | 1 | 1 |
| CALONE CAM (1%) | 2 | 2 |
| METHIONONE GAMMA COEUR ™ | 3 | 3 |
| Dipropylene glycol | 5 | — |
| 3-hexenyl 2-methylallyl ether (Z) | — | 5 |
| Total | 195 | 195 |

Formulation II was found to be more floral, smoother, greener and stronger with 3-hexenyl 2-methyallyl ether than Formulation I which did not contain it.

EXAMPLE 3

Another fragrance was prepared incorporating the compound of the present invention.

0.15 Acetyl Iso Eugenol
19.65 Benzyl Salicylate
50.00 Galaxolide IPM 50 PCT
11.00 Hydroxycitronellal Extra
11.00 Iso E super
3.00 Phenyl Ethyl Alcohol
5.00 Terpineol Coeur
+b 0.20 Ether,+b 3-Hexenyl +b 2-Methylallyl,(Z)
100.0 Total The fragrance was found to possess a unique, leafy green and metallic note. The fragrance was also described as powerful.

What is claimed is:

1. A compound having the formula

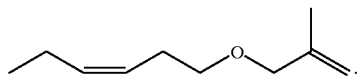

2. The compound of claim 1 incorporated in perfumes, colognes, toilet water, candles, air fresheners and personal care products.

3. The compound of claim 2 wherein the personal care product is selected from the group consisting of detergents, dishwashing compositions, scrubbing compounds and window cleaners.

4. A method for perfuming a product by incorporating an olfactory acceptable amount of the compound of claim 1.

5. The method of claim 4 wherein the product is a perfume, cologne, toilet water, candle, air freshener or personal care product.

6. The method of claim 5 wherein the personal care product is selected from the group consisting of detergents, dishwashing compositions, scrubbing compounds and window cleaners.

7. The Z isomer of compound of claim 1.

* * * * *